United States Patent [19]
Anand

[11] Patent Number: 5,825,563
[45] Date of Patent: Oct. 20, 1998

[54] MIRROR AND SUPPORT FOR USE IN A MAGNETIC RESONANCE IMAGING DEVICE

[75] Inventor: Prem K. Anand, Roswell, Ga.

[73] Assignee: General Electric Company, Milwaukee, Wis.

[21] Appl. No.: 527,022

[22] Filed: Sep. 12, 1995

[51] Int. Cl.⁶ .............................. G02B 7/182; A61G 13/12
[52] U.S. Cl. .......................... 359/872; 359/881; 378/209; 5/601
[58] Field of Search ..................................... 359/862, 871, 359/872, 881, 884; 378/209; 5/600, 601

[56] References Cited

U.S. PATENT DOCUMENTS

| | | | |
|---|---|---|---|
| 1,951,214 | 3/1934 | Schlumbohn | 359/884 |
| 3,019,689 | 2/1962 | Paulsrud | 359/879 |
| 4,287,422 | 9/1981 | Kuphal et al. | 378/209 |
| 4,531,813 | 7/1985 | Van den Berg | 359/862 |
| 4,650,299 | 3/1987 | Stevens et al. | 359/862 |
| 4,696,030 | 9/1987 | Egozi . | |
| 4,804,261 | 2/1989 | Kirschen | 351/50 |
| 4,901,141 | 2/1990 | Costello . | |
| 4,923,295 | 5/1990 | Sireul et al. | 359/881 |
| 5,076,275 | 12/1991 | Bechor et al. | 128/653.2 |
| 5,134,373 | 7/1992 | Tsuruno et al. | 359/872 |
| 5,185,778 | 2/1993 | Magram | 378/209 |
| 5,277,184 | 1/1994 | Messana . | |
| 5,339,813 | 8/1994 | DeYoe et al. . | |
| 5,355,885 | 10/1994 | Tsuda et al. . | |

OTHER PUBLICATIONS

Nuclear Associates, "New! Hi–Tech MRI Video System" brochure.
Avotec, "Silent Vision" brochure.
Nuclear Associates, "MRI Patient Relaxation Systems!" brochure.
Nuclear Associates, "Advanced High–Tech Plus MRI Audio System" brochure.
Nuclear Associates, "MRI Patient Alert System" brochure.

Primary Examiner—Ricky D. Shafer
Attorney, Agent, or Firm—Thomas, Kayden, Horstemeyer & Risley; John H. Pilarski

[57] ABSTRACT

A mirror for use in a magnetic resonance imaging (MRI) apparatus is mounted above a bed of the MRI apparatus. The mirror is mounted onto a support arm that extends above and over the bed. The support arm is preferably transparent so as to minimize the amount of claustrophobic feelings induced in a patient. The support arm is attached at a lower end onto a base and also has teeth for insertion within a channel of the bed. The base has a ridge which is inserted into a second channel of the bed and has a post with a cam-shaped end for locking the mirror to the bed. The mirror can be moved to any location along the length of the bed and can also be moved to either side of the bed. Consequently, the location of the mirror can be easily adjusted according to the position of the patient so that the patient will always receive images reflected off of the mirror.

6 Claims, 2 Drawing Sheets

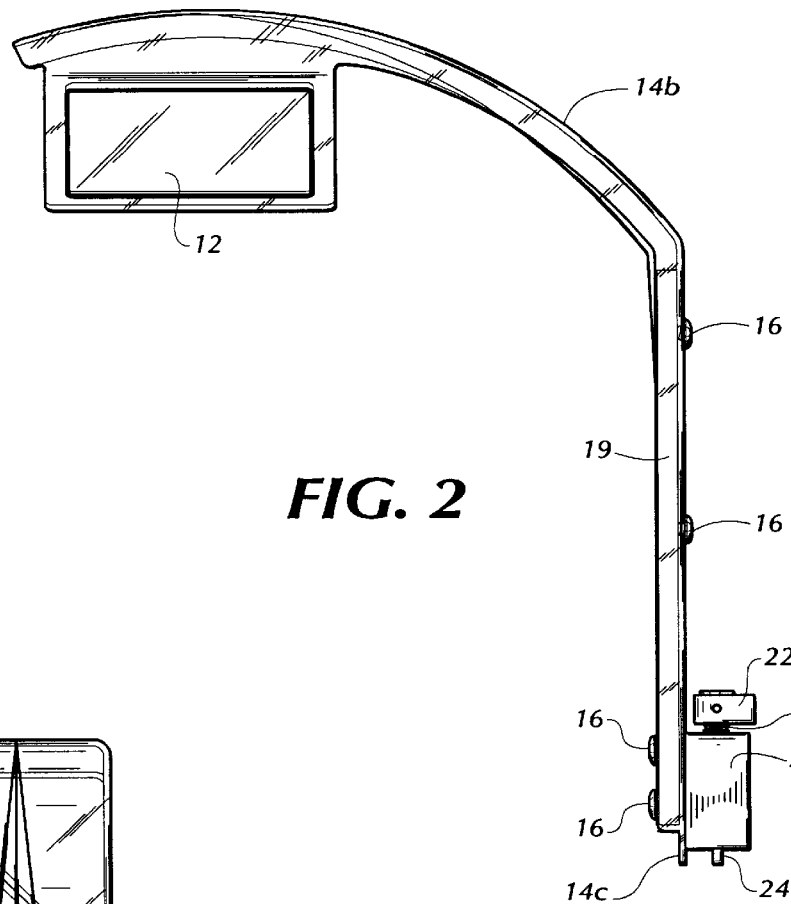
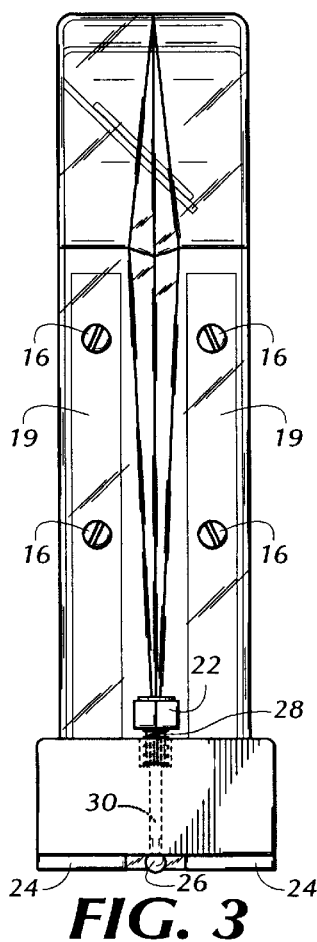
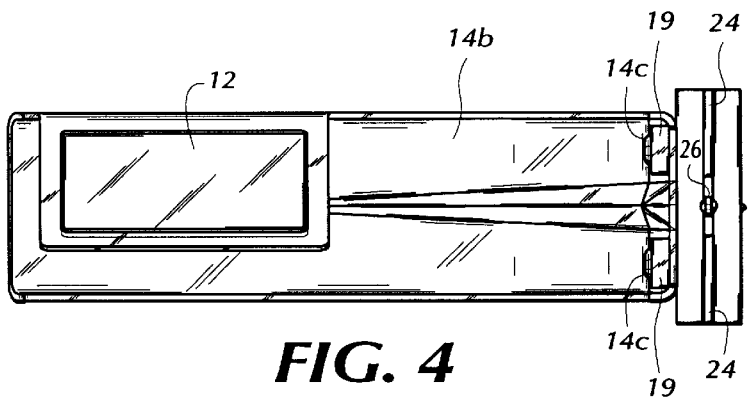

MIRROR AND SUPPORT FOR USE IN A MAGNETIC RESONANCE IMAGING DEVICE

BACKGROUND OF THE INVENTION

1. Field of the Invention

The present invention generally relates to a mirror and, more particularly, to a mirror and support for use with a magnetic resonance imaging device.

2. Description of the Prior Art

With a typical magnetic resonance imaging (MRI) apparatus, a patient is placed onto a bed and the bed is slid into a bore extending through the center of the device. After the patient is positioned within the MRI apparatus, a procedure is initiated for acquiring a number of images of the patient. This procedure for acquiring images is a rather long process, such as forty minutes to an hour, during which the patient must remain as still as possible. Any motion from the patient can degrade the quality of the images and, if the quality of the images are too poor, an additional imaging procedure may be required.

The central bore of the MRI apparatus is very small and can easily induce claustrophobic feelings in the patient. As is known in the art, these claustrophobic feelings may be reduced or even completely eliminated by providing the patient with some type of entertainment during the imaging procedure. Accordingly, many types of entertainment systems have been designed to provide the patient with visual images in order to distract the patient from the imaging procedure.

In view of the magnetic fields generated by the MRI apparatus, any entertainment system operating in the vicinity of these fields must have suitable shielding. Conversely, the entertainment systems must not generate any stray magnetic fields since the MRI apparatus is very susceptible to even low level magnetic fields. Consequently, some entertainment systems have been designed to generate images at a distance away from the MRI apparatus and then direct the images into the bore for the patient's viewing pleasure.

One manner in which images are directed to the patient is by generating the images with some type of display panel spaced from the MRI apparatus and then reflecting the images into the eyes of the patient. An example of this type of entertainment system is disclosed in U.S. Pat. No. 5,134,373 and in U.S. Pat. No. 5,076,275 to Bechor et al. The entertainment systems in these patents employ a non-magnetic mirror mounted within the bore of the MRI apparatus for reflecting images from behind the patient down into the eyes of the patient.

A problem with these mirrors is that their positions are fairly fixed. While a patient may be able to adjust the angle of these mirrors, the position of the mirrors within the bore is otherwise fixed. For instance, the position of this type of mirror is fixed along the axis of the bore. Since the patient may not always be in the same position within the bore of the MRI apparatus, the patient may be unable to view images from the display panel. Also, certain MRI procedures may require that the patient be inserted from the opposite end of the MRI apparatus, such as head-first rather than feet-first. Unless the MRI apparatus was equipped with two mirrors, the patient would be unable to view the display panel when the patient is inserted from the opposite end of the MRI apparatus. Thus, it is a problem for this type of mirror to reflect images into the eyes of the patient for the variety of different positions in which a patient may be placed within the MRI apparatus.

Another type of mirror for reflecting images from behind the patient into the eyes of the patient is produced by MRI Associates and is mounted directly onto the moveable bed. The mirror is positioned above the patient's head and is mounted onto a frame that has arms that attach to either side of the bed. A disadvantage of this mirror is that the support structure for the mirror, which includes the arms, surrounds the patient's head and can actually contribute to the patient's claustrophobic feelings. Additionally, the mirror is securely fastened to the bed and is not easily moved to another position.

A need therefore exists for a mirror that can have its position adjusted according to the location of the patient. A need also exists for a mirror which does not contribute to the patient's claustrophobic feelings and which additionally can be easily moved to a new location.

SUMMARY OF THE INVENTION

An object of the present invention is to provide a mirror which can have its position adjusted relative to a longitudinal axis of a MRI device.

Another object of the present invention is to provide a mirror which minimizes the claustrophobic feelings of a patient.

Another object of the present invention is to provide a mirror which can have its position easily adjusted.

Additional objects, advantages, and novel features of the invention will be set forth in the description which follows, and will become apparent to those skilled in the art upon reading this description or practicing the invention.

To achieve the foregoing and other objects, a novel mirror for use in a magnetic resonance imaging (MRI) apparatus comprises a reflective member for directing light from behind or in front of a patient down into eyes of the patient. The reflective member is mounted to a support arm which positions the reflective member above the eyes of the patient. The support arm is mounted to a bed of the MRI device and is comprised of a transparent material for minimizing the amount of claustrophobic feelings that are induced in the patient.

In another aspect of the invention, a device for mounting an element to the bed of a magnetic resonance imaging apparatus comprises a base having a bottom for resting on the bed and at least one ridge for insertion within the channel of the bed. A post extends through the base, has an enlarged distal end for insertion within the channel, and has a knob integral with its proximal end. The distal end of the post is shaped to have a width which is no greater than a width of the channel and a length which is greater than the width of the channel. The element is mounted to the base and the base is then mounted to the bed by first inserting the distal end of the post into the channel so that the distal end passes a ledge which defines the channel width. By rotating the knob 90 degrees, the post is rotated so that the length of the distal end becomes transverse to the longitudinal axis of the channel and so that the distal end engages the lower surface of the ledge, thereby locking the device to the bed of the MRI apparatus. The element mounted to the bed is preferably a reflective member.

In the preferred embodiment, the reflective member is a planar sheet of glass having an optical filtering material. The reflective member is mounted with a support arm that extends above and over the bed of the MRI apparatus.

Because the device is mounted on the bed in the near vicinity of the MRI apparatus, the device is comprised of non-magnetic materials so that the device does not interfere with the imaging procedure.

BRIEF DESCRIPTION OF THE DRAWINGS

The accompanying drawings, which are incorporated in, and form a part of, the specification, illustrate a preferred embodiment of the present invention and, together with the description, serve to explain the principles of the invention. The drawings are not necessarily to scale, emphasis instead being placed upon clearly illustrating the principles of the invention. In the drawings:

FIG. 2 is a front plan view of the mirror of FIG. 1;

FIG. 3 is a side view of the mirror of FIG. 1; and

FIG. 4 is a bottom view of the mirror of FIG. 1.

DETAILED DESCRIPTION OF THE PREFERRED EMBODIMENT

Figure 1:
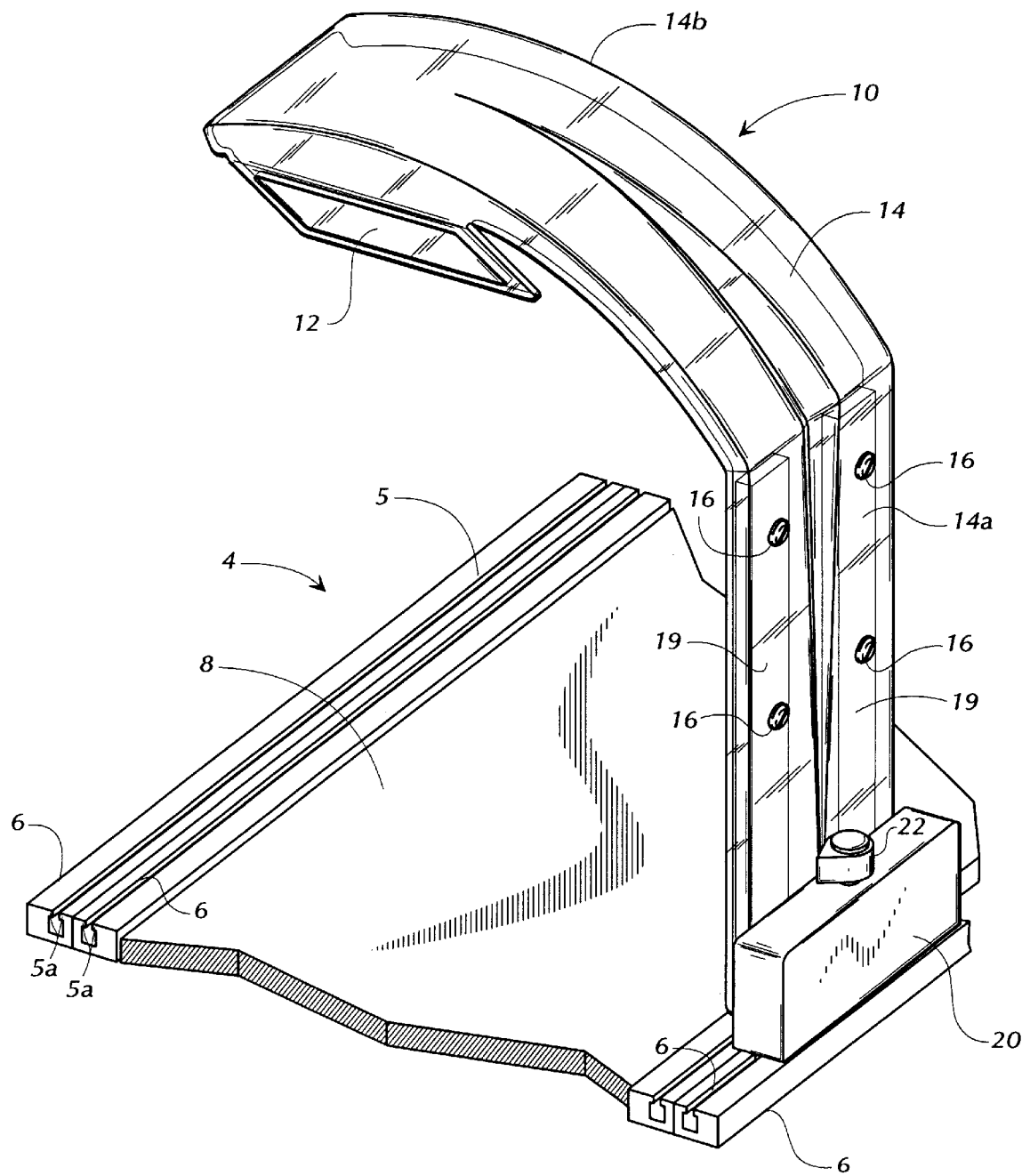
FIG. 1 is a perspective view of a mirror according to a preferred embodiment of the invention attached to a moveable bed of a magnetic resonance imaging device.

Reference will now be made in detail to the preferred embodiment of the invention. With reference to FIG. 1, a mirror 10 according to the invention is shown as being attached to a moveable bed 4 of a magnetic resonance imaging (MRI) apparatus. A rail 5 is disposed on either side of the bed 4 and has a pair of channels 6 formed along the longitudinal axis of the bed 4. The bed 4 also has a cushion or pad 8 for supporting a patient. As is common in the industry, the patient is placed on the bed 4 and then the bed 4 is slid into a central bore of the MRI apparatus in order to position the patient within the MRI apparatus. After the completion of an imaging procedure, the bed 4 and the patient are withdrawn from the central bore of the MRI apparatus.

During the imaging procedure, it is desirable to distract the patient by supplying the patient with images, such as those from a display panel. These images can entertain the patient and can also reduce claustrophobic feelings in the patient. The images may also include information about the imaging procedure, such as the remaining amount of time in the imaging procedure or whether the MRI device is actively acquiring images of the patient. Although the mirror 10 may be used to reflect any type of image, the mirror 10 will be described as being used with an entertainment system that generates video images with a display panel.

The mirror 10 has a reflective surface 12 which is angled for reflecting images down toward the bed 4 and into the eyes of the patient. The reflective surface 12 is preferably a piece of glass comprised of an optical filtering material which is highly reflective for the wavelengths of visible light. A suitable mirror is a multi-layer dielectric 45 degrees cold mirror. The reflective surface 12 may be comprised from any suitable reflective material which is additionally non-magnetic and non-metallic. The invention, however, is not limited to a reflective surface 12 but encompasses other types of devices or materials for directing images into the eyes of the patient, such as a prism.

The reflective surface 12 is glued or otherwise attached to a support arm 14, which has one end attached to a base 20. The support arm 14 is comprised of a transparent plastic material and is preferably a polycarbonate, such as Lexan.® Because the patient can direct his or her gaze substantially through the support arm 14, the arm 14 minimizes the claustrophobic feelings in the patient. In general, the arm 14 has a vertically extending portion 14a and a horizontally extending portion 14b. The arm 14, however, is not limited to this exact shape but may be formed in other shapes which place the reflective surface 12 over the bed 4.

As better seen in FIGS. 2 to 4, the support arm 14 is attached to the base 20 and also to a pair of stiffening bars 19. Each stiffening bar 19 extends across substantially the entire length of the vertical portion 14a of the arm 14 and is attached to the vertical portion 14a of the arm 14 at four different locations. With reference to FIG. 2, a set of screws 16 attach each stiffening bar 19 to the arm 14 at two locations above the base 20 and also attach each stiffening bar 19 at two different locations to the base 20. The stiffening bars 19 are comprised of a transparent plastic material, preferably the polycarbonate Lexan®, provide support for the arm 14, and also assist in the securing of the arm 14 to the base 20.

A pair of teeth 14c are formed integrally with the bottom of the vertical portion 14a of the arm 14 and, as shown in FIG. 4, are substantially aligned with bottoms of the stiffening bars 19. When the mirror 10 is mounted onto the bed 4, both of the teeth 14c are inserted into the channel 6 which is located closer to the pad 8. The teeth 14c have a width which is sufficiently large to firmly engage either side of the channel 6 when the mirror 10 is mounted onto the bed 4 and which also permits the detachment of the mirror 10 from the bed 4. The bottom of base 20 bears the weight of the entire mirror 10 when the mirror 10 is mounted onto the bed 4.

The base 20 is also used to mount the mirror 10 to the bed 4. The base 20 has a pair of ridges 24 that are inserted into the channel 6 furthest away from the pad 8. As with the teeth 14c, the width of the ridges 24 is such to firmly engage either side of the channel 6 when the mirror 10 is mounted onto the bed 4 but allows the removal of the mirror 10 from the bed 4 when a removal force is exerted onto the mirror 10.

With reference to FIGS. 3 and 4, a locking post 30 projects down through the center of the base 20 and has a cam 26 aligned with the ridges 24. A spring 28 is located between the base 20 and a knob 22 and biases the locking post 30 and cam 26 in an upward position, which is the position shown in FIG. 3. The base 20 has a centrally formed bore for receiving the post 30 with the bore having a diameter smaller than the width of cam 26. The upward travel of the post 30 is therefore limited by contact between the cam 26 and the bottom of the base 20.

To mount the mirror 10 to the bed 4, the cam 26 and the ridges 24 are placed into the outer channel 6 while the teeth 14c are placed into the inner channel 6. Next, the knob 22 is pressed down so that the cam 26 is lowered beneath horizontally extending ledges 5a in the rail 5 and is then rotated 90 degrees so that the cam 26 becomes perpendicular to the length of the rail 5. After releasing the knob 22, the spring 28 biases the locking post 30 and cam 26 upwardly and causes the cam 26 to engage the lower surfaces of the ledges 5a, thereby locking the mirror 10 onto the bed 4. To unlock the mirror 10 from the bed 4, the knob 22 is pressed down and rotated another 90 degrees, thereby aligning the cam 26 with the channel 6 and permitting the removal of the mirror 10 from the bed 4.

Because the mirror 10 is positioned within the central bore of the MRI apparatus, the mirror 10 must be comprised of non-magnetic and non-metallic materials. Accordingly, as set forth above, the arm 14 and stiffening bars 19 are comprised of a polycarbonate material. The screws 16 and the base 20 are comprised of a nylon or similar type of plastic material, preferably Delrin®, the spring 28 is comprised of beryllium copper, and the locking post 30 and cam 26 are comprised of aluminum. The invention, however, is not limited to these materials and, as will be apparent to those skilled in the art, may be comprised of other non-magnetic materials.

The mirror 10 according to the invention may be easily placed at any location along the length of the bed 4 and can therefore be adjusted according to the position of the patient. The mirror 10 can also be mounted onto either side of the bed 4 whereby the mirror 10 may be used to direct images into the eyes of the patient regardless of whether the patient is positioned head-first or feet-first into the MRI apparatus.

Advantageously, the arms 14 and stiffening bars 19, which form a major portion of the entire mirror 10, are formed from a transparent material. Since the patient can direct his or her gaze through the arm 14 and bars 19, the amount that the mirror 10 induces claustrophobic feelings in the patient can be minimized.

The foregoing description of the preferred embodiment of the invention has been presented for purposes of illustration and description. It is not intended to be exhaustive or to limit the invention to the precise form disclosed. Many modifications and variations are possible in light of the above teaching.

For example, the arm 14 may be mounted to the base 20 in manners other than that described, such as to the top of the base 20. Further, the base 20 may be attached to both channels 6 and could therefore have two sets of ridges 24 for insertion into the two channels 20. Also, the base 20 may be used to mount other types of items, such as an IV stand, to the bed 4. The IV stand may be mounted along with, or separately, from the arm 14 and reflective surface 12 and may be formed from a non-magnetic material, such as brass, stainless steel, or aluminum. Also, the reflective surface 12 may have its angle adjustable, such as by permitting rotational movement between portion 14*b* and portion 14*a* of the arm 14.

The embodiment was chosen and described in order to explain the principles of the invention and their practical application to thereby enable others skilled in the art to utilize the invention and various embodiments and with various modifications as are best suited to the particular use contemplated. It is intended that the scope of the invention be defined by the claims.

I claim:

1. A reflecting device for use in a magnetic resonance imaging apparatus, comprising:

a reflective member for directing light from behind a patient down into eyes of the patient;

a support arm, attached to said reflective member, for positioning said reflective surface above the eyes of the patient; and means for mounting said support arm to a bed of said magnetic resonance imaging apparatus;

wherein said support arm is comprised of a transparent material for minimizing an amount said reflecting device induces claustrophobic feelings in said patient, said mounting means has at least one ridge for being inserted into a channel formed along a longitudinal axis of said bed, and said support arm has at least one ridge for being inserted into a second channel formed along said longitudinal axis of said bed.

2. A device for mounting an element to a bed of a magnetic resonance imaging apparatus wherein the bed has a channel formed along a longitudinal axis of said bed, said device comprising:

a base having a bottom for resting on said bed and at least one ridge for insertion within said channel of said bed;

a post extending through said base and having an enlarged distal end for insertion within said channel, said distal end of said post having a width no greater than a width of said channel but having a length which is greater than said width of said channel;

a knob integral with a proximal end of said post and is for rotating said post upon rotation of said knob; and means for mounting said element to said base;

wherein said device is mounted to said bed by inserting said distal end into said channel past a ledge defining said width of said channel with said length of said distal end being parallel to said longitudinal axis of said channel and then rotating said knob so that said length of said distal end becomes transverse to said longitudinal axis of said channel and so that said distal end engages said ledge.

3. The device as set forth in claim 2, wherein said element comprises a reflective surface for directing light down onto said bed.

4. The device as set forth in claim 3, wherein said mounting means comprises an arm having a first portion extending up from said bed and a second portion extending over said bed, said reflective surface being attached to said second portion so that said reflective surface is positioned over said bed.

5. The device as set forth in claim 4, wherein said arm is comprised of a transparent material.

6. The device as set forth in claim 2, further comprising means for biasing said post away from said bed so that said distal end of said post firmly engages said ledge when said device is mounted to said bed.

* * * * *